(12) United States Patent
Drake et al.

(10) Patent No.: US 8,920,432 B2
(45) Date of Patent: Dec. 30, 2014

(54) LEAD DELIVERY DEVICE AND METHOD

(75) Inventors: Ronald Alan Drake, Saint Louis Park, MN (US); Lindsey Marie Tobin, Minneapolis, MN (US); Stanten C. Spear, Arden Hills, MN (US); Scott William Hayden, Maple Grove, MN (US); Andrea Jean Asleson, Maple Grove, MN (US); Steven Lawrence Waldhauser, White Bear Township, MN (US); Kendra Yasger, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1462 days.

(21) Appl. No.: 12/474,425

(22) Filed: May 29, 2009

(65) Prior Publication Data

US 2009/0326550 A1 Dec. 31, 2009

Related U.S. Application Data

(63) Continuation-in-part of application No. 12/183,401, filed on Jul. 31, 2008, and a continuation-in-part of application No. 12/183,105, filed on Jul. 31, 2008.

(60) Provisional application No. 61/076,183, filed on Jun. 27, 2008.

(51) Int. Cl.
| | |
|---|---|
| *A61N 1/05* | (2006.01) |
| *A61B 17/00* | (2006.01) |
| *A61B 17/22* | (2006.01) |
| *A61M 25/04* | (2006.01) |
| *A61M 25/09* | (2006.01) |

(52) U.S. Cl.
CPC ....... *A61N 1/056* (2013.01); *A61B 2017/22047* (2013.01); *A61N 2001/0585* (2013.01); *A61M 25/04* (2013.01); *A61B 2017/22048* (2013.01); *A61M 2025/09183* (2013.01)
USPC .......................................... 606/129; 607/122

(58) Field of Classification Search
None
See application file for complete search history.

(56) References Cited

U.S. PATENT DOCUMENTS

| | | | |
|---|---|---|---|
| 4,497,326 | A | 2/1985 | Curry |
| 4,619,246 | A | 10/1986 | Molgaard-Nielsen et al. |
| 5,147,377 | A | 9/1992 | Sahota |
| 5,167,239 | A | 12/1992 | Cohen et al. |

(Continued)

FOREIGN PATENT DOCUMENTS

EP 0 861 676 A2 9/1998

OTHER PUBLICATIONS (PCT/US2009/050783) PCT Notification of Transmittal of the International Search Report and the Written Opinion of the International Searching Authority, 15 pages, Mar. 3, 2010.

*Primary Examiner* — Kennedy Schaetzle
*Assistant Examiner* — Erica Lee
(74) *Attorney, Agent, or Firm* — Carol F. Barry

(57) ABSTRACT

A medical apparatus includes a guidewire and a fixator catheter. The fixator catheter comprises a tubular body with a distal portion and a proximal portion, and further includes a distal opening, a fixator secured to the distal portion, and a body opening arranged between the fixator and the proximal portion. The guidewire passes through the body opening and the distal opening of the fixator catheter. The fixator is movable between a compact configuration and an expanded configuration and, in the expanded condition, is capable of anchoring the guidewire and fixator catheter in a lumen of a blood vessel.

6 Claims, 17 Drawing Sheets

(56) References Cited

U.S. PATENT DOCUMENTS

| | | |
|---|---|---|
| 5,181,911 A | 1/1993 | Shturman |
| 5,224,491 A | 7/1993 | Mehra |
| 5,265,622 A | 11/1993 | Barbere |
| 5,279,299 A | 1/1994 | Imran |
| 5,364,340 A | 11/1994 | Coll |
| 5,437,083 A | 8/1995 | Williams et al. |
| 5,449,372 A | 9/1995 | Schmaltz et al. |
| 5,456,667 A | 10/1995 | Ham et al. |
| 5,456,705 A | 10/1995 | Morris |
| 5,474,563 A | 12/1995 | Myler et al. |
| 5,549,553 A | 8/1996 | Ressemann et al. |
| 5,653,684 A | 8/1997 | Laptewicz et al. |
| 5,693,014 A | 12/1997 | Abele et al. |
| 5,833,707 A | 11/1998 | McIntyre et al. |
| 5,954,761 A | 9/1999 | Machek et al. |
| 6,010,498 A | 1/2000 | Guglielmi |
| 6,014,589 A | 1/2000 | Farley et al. |
| 6,122,552 A | 9/2000 | Tockman et al. |
| 6,152,946 A | 11/2000 | Broome et al. |
| 6,161,029 A | 12/2000 | Spreigl et al. |
| 6,196,230 B1 | 3/2001 | Hall et al. |
| 6,322,559 B1 | 11/2001 | Daulton et al. |
| 6,331,190 B1 | 12/2001 | Shokoohi et al. |
| 6,415,187 B1 | 7/2002 | Kuzma et al. |
| 6,595,989 B1 | 7/2003 | Schaer |
| 6,602,271 B2 | 8/2003 | Adams et al. |
| 6,697,677 B2 | 2/2004 | Dahl et al. |
| 6,928,313 B2 | 8/2005 | Peterson |
| 6,931,286 B2 | 8/2005 | Sigg et al. |
| 6,970,742 B2 | 11/2005 | Mann et al. |
| 7,107,105 B2 | 9/2006 | Bjorklund et al. |
| 2003/0225434 A1 | 12/2003 | Glantz et al. |
| 2004/0059348 A1 | 3/2004 | Geske et al. |
| 2004/0116878 A1 | 6/2004 | Byrd et al. |
| 2004/0162599 A1 | 8/2004 | Kurth |
| 2004/0215298 A1 | 10/2004 | Richardson et al. |
| 2005/0113862 A1 | 5/2005 | Besselink et al. |
| 2006/0106445 A1 | 5/2006 | Woollett |
| 2006/0292912 A1 | 12/2006 | Bjorklund et al. |
| 2007/0043413 A1 | 2/2007 | Eversull et al. |
| 2007/0079511 A1 | 4/2007 | Osypka |
| 2007/0100409 A1 | 5/2007 | Worley et al. |
| 2007/0100410 A1* | 5/2007 | Lamson et al. ............ 607/119 |
| 2008/0103537 A1 | 5/2008 | Sigg et al. |
| 2008/0103575 A1 | 5/2008 | Gerber |

* cited by examiner

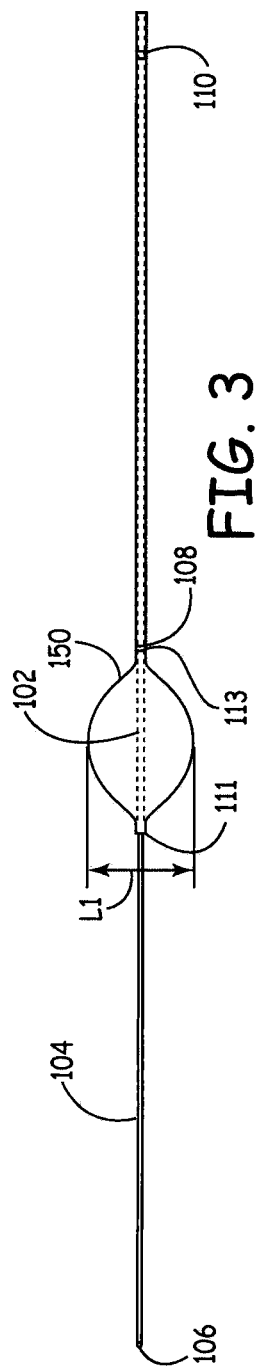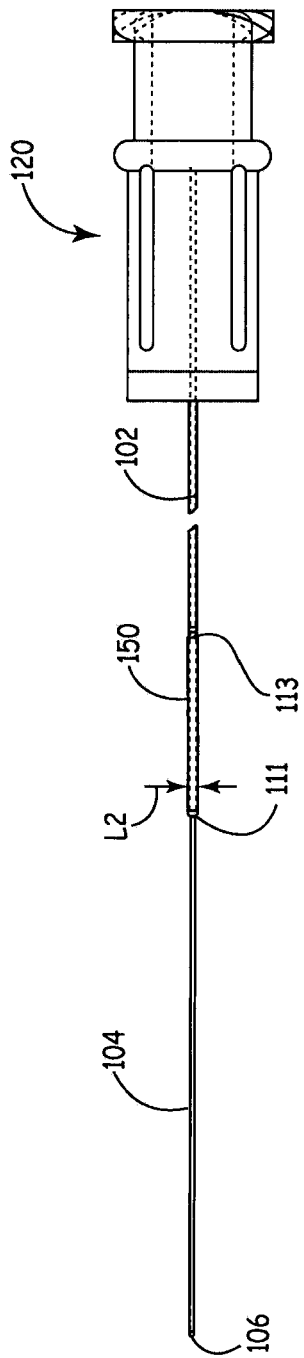

LEAD DELIVERY DEVICE AND METHOD

CROSS-REFERENCE TO RELATED APPLICATIONS

This application is a continuation-in-part of U.S. Ser. No. 12/183,401, filed Jul. 31, 2008, which claims the benefit of U.S. Provisional Application No. 61/076,183, filed on Jun. 27, 2008.

This application is a continuation-in-part of U.S. Ser. No. 12/183,105, filed Jul. 31, 2008, which claims the benefit of U.S. Provisional Application No. 61/076,183, filed on Jun. 27, 2008.

This application is related to U.S. patent application Ser. No. 12/4744,466 filed concurrently herewith, entitled "Lead Delivery Device and Method."

This application is related to U.S. patent application Ser. No. 11/468,910 filed on Aug. 31, 2006, which is a division of U.S. patent application Ser. No. 10/254,196, filed on Sep. 24, 2002, now U.S. Pat. No. 7,107,105.

The disclosures of the above applications are incorporated herein by reference.

INTRODUCTION

Various cardiac devices providing electrical stimulation, rhythm management, or resynchronization therapy to the heart include implantable electrically conductive leads in contact with excitable heart or other body tissue.

The present teachings provide a device and method for delivering an implantable electrically conductive lead to a target site for a use with a cardiac device.

SUMMARY

The present teachings provide a medical apparatus that includes an implantable electrically conductive lead for a cardiac device, the lead having an internal bore terminating at a distal lead opening, and a lead delivery device for delivering the distal end of the lead to a blood vessel during implantation of the lead. The lead delivery device includes a removably anchorable guidewire, and a fixator attached to a distal portion of the guidewire for anchoring the guidewire. The fixator is movable between a compact configuration and an expanded configuration. The fixator is capable of passing through the distal lead opening of the lead in the compact configuration. The fixator is capable of exerting a holding force in the range of about 0.89 to 4.45 N in the lumen of the blood vessel in the expanded configuration.

The present teachings also provide a medical method that includes inserting a distal end of cannulated catheter through cardiac tissue into a main cardiac vessel, attaching an expandable fixator to a distal portion of a guidewire, inserting the guidewire through the catheter, advancing the guidewire past the distal end of the catheter and into a target site in a lumen of a branching vessel, expanding the fixator into the target site, removably anchoring the fixator into the lumen with a holding force in the range of about 0.89 to 4.45 N, and removing the catheter. The method further includes advancing an implantable electrically conductive lead of a cardiac device over the guidewire to the target site without moving the guidewire while tensioning the guidewire, and delivering the distal portion of the lead at the target site.

In another aspect, the present teachings provide a medical apparatus that includes a cardiac device for providing cardiac therapy, or cardiac sensing, or a combination thereof, an implantable electrically conductive lead having proximal and distal ends, the proximal end couplable to the cardiac device, the lead having an internal bore terminating at a distal opening at the distal end, and a lead delivery device for delivering the distal end of the lead to a blood vessel during implantation of the lead. The lead delivery device includes a removably anchorable guidewire, and a fixator attached to a distal portion of the guidewire, the fixator movable between a compact configuration and an expanded configuration. The fixator has a compact width less or equal to about 0.483 mm and is capable of passing through the distal lead opening of the lead in the compact configuration. The fixator has an expanded width up to about 5 mm, and is capable of exerting a holding force in the range of about 0.89 to 4.45 N in the lumen of the blood vessel in the expanded configuration.

In a further aspect, the present teachings provide a medical apparatus comprising a guidewire and a fixator catheter. The fixator catheter comprises a tubular body with a distal portion and a proximal portion. The fixator catheter further comprises a distal opening, a fixator secured to the distal portion, and a body opening arranged between the fixator and the proximal portion. The guidewire is passed through the body opening and the distal opening of the fixator catheter. The fixator is movable between a compact configuration and an expanded configuration.

In yet another aspect, the present teachings provide a medical method comprising passing a guidewire through a fixator catheter. The fixator catheter comprises a tubular body with a distal portion and a proximal portion. The fixator catheter further comprises a distal opening, a fixator secured to the distal portion, and a body opening arranged between the fixator and the proximal portion. The guidewire is passed through the body opening and the distal opening of the fixator catheter. The method further comprises navigating the guidewire and fixator catheter to a desired site. At the desired site, the fixator is expanded to an expanded configuration in order to releasably secure the fixator catheter. An implantable electrically conductive lead of a cardiac device is advanced over the guidewire to the desired site while the fixator is deployed.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 3 is a plan view of a lead delivery device having a fixator according to the present teachings, the lead delivery device shown with the fixator in an expanded configuration;

FIG. 4 is a plan view of a lead delivery device having a fixator according to the present teachings, the lead delivery device shown with the fixator in a compact configuration;

DESCRIPTION OF VARIOUS ASPECTS

Figure 1:
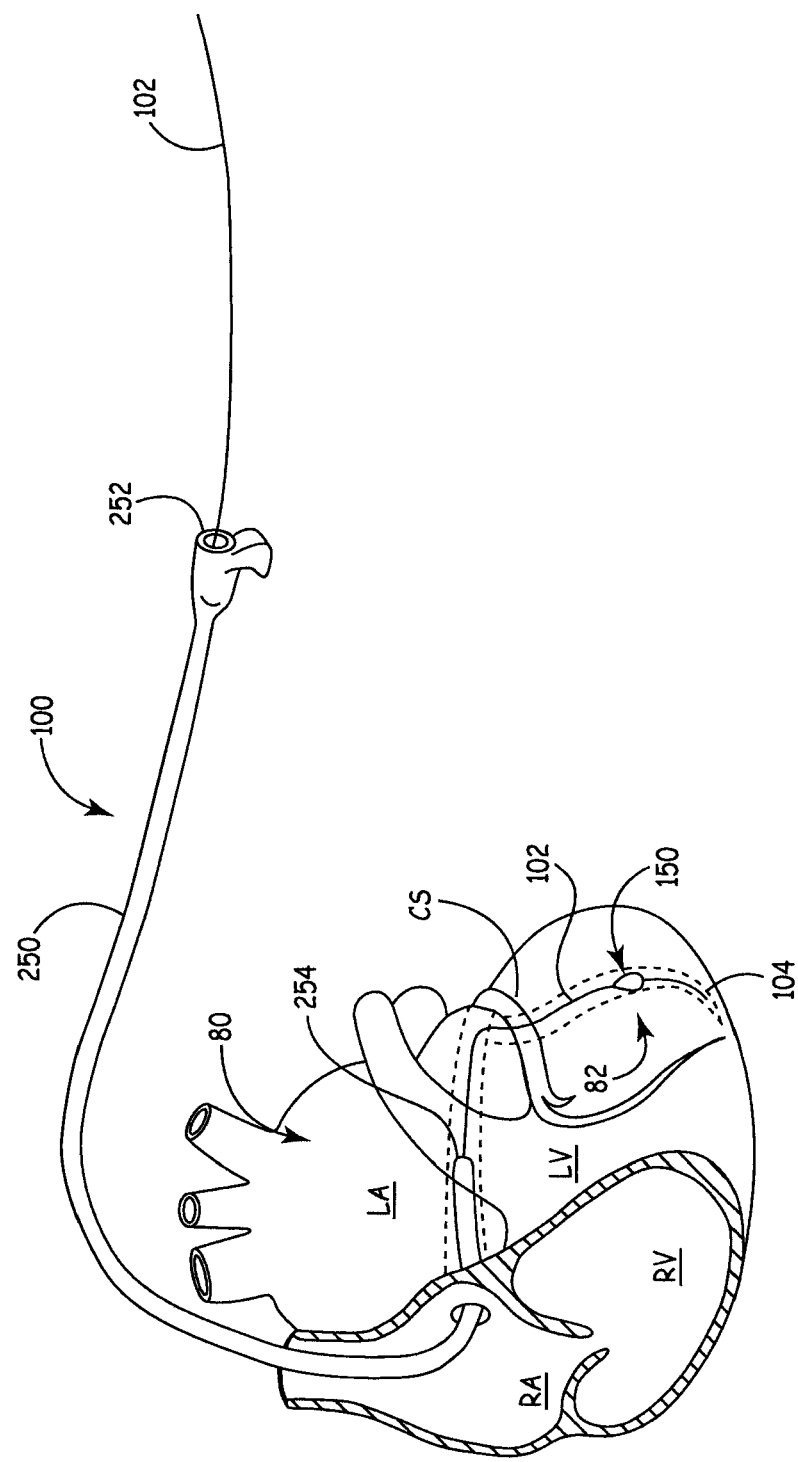
FIG. 1 is an environmental view of a lead delivery device according to various embodiments of the present teachings.

The following description is merely exemplary in nature and is in no way intended to limit the present teachings, applications, or uses. The present teachings are applicable to any devices that require implantation of electrically conductive leads, including pacemakers, defibrillators or other cardiac devices providing rhythm management, resynchronization therapy or other cardiac therapy.

During left heart (LH) lead delivery methods for implanting cardiac therapy devices, cannulated catheters can be used to provide support and stiffness and allow trackability of the lead into the coronary sinus and more acute branching vessels. For example, in Cardiac Resynchronization Therapy (CRT), a special third lead is implanted via the Coronary Sinus (CS) and positioned in a sub-selected cardiac vein to sense and/or pace the left ventricle in combination with atrial-synchronized, biventricular pacing using standard pacing technology. Following a sensed atrial contraction or atrial-paced event, both ventricles are stimulated to synchronize their contraction. The resulting ventricular resynchronization reduces mitral regurgitation and optimizes left ventricular filling, thereby improving cardiac function.

Guidewires can be used inside the Coronary Sinus and Great Cardiac Vein to gain access to acute side branches. A guidewire is placed into the targeted vessel and the lead is placed over the guidewire and through the catheter. Under existing methods, during lead delivery, a compressive force is maintained by a forward pressure on both the guidewire and lead to allow the lead to travel distally in the branching veins at the target site. The lead itself is designed to provide stiffness and steerability characteristics for the purpose of placement into the vessels. After the LH lead has reached its desired location, the delivery catheters used during the procedure must be removed by slitting because the proximal end of the lead is larger in diameter than the bore of the catheter and the catheter cannot be removed over the lead. The slitting procedure requires a very specific skill set, provides multiple avenues for user error and places constraints on catheter design, construction and use.

In contrast to the existing method described above, the present teachings provide a lead delivery device method that does not require slitting the catheter. The lead delivery device includes a guidewire that can be temporarily anchored in a sub-selected acute coronary vein branch during lead delivery. Fixation can be provided by a fixator that expands from a compact configuration of very low profile fitting inside a lead to an expanded configuration having a dimension large enough to allow sufficient tension to be placed on the guidewire to enable lead delivery over the guidewire in a zip-line or rope-climbing manner, as described below. The guidewire with the fixator in the compact configuration can be guided through the catheter to the target site. The catheter can then be removed before the lead is advanced over the guidewire. After the lead is implanted, the fixator is returned to the compact configuration and removed together with the guidewire through the implanted lead without slitting.

Figures 1A, 1B:
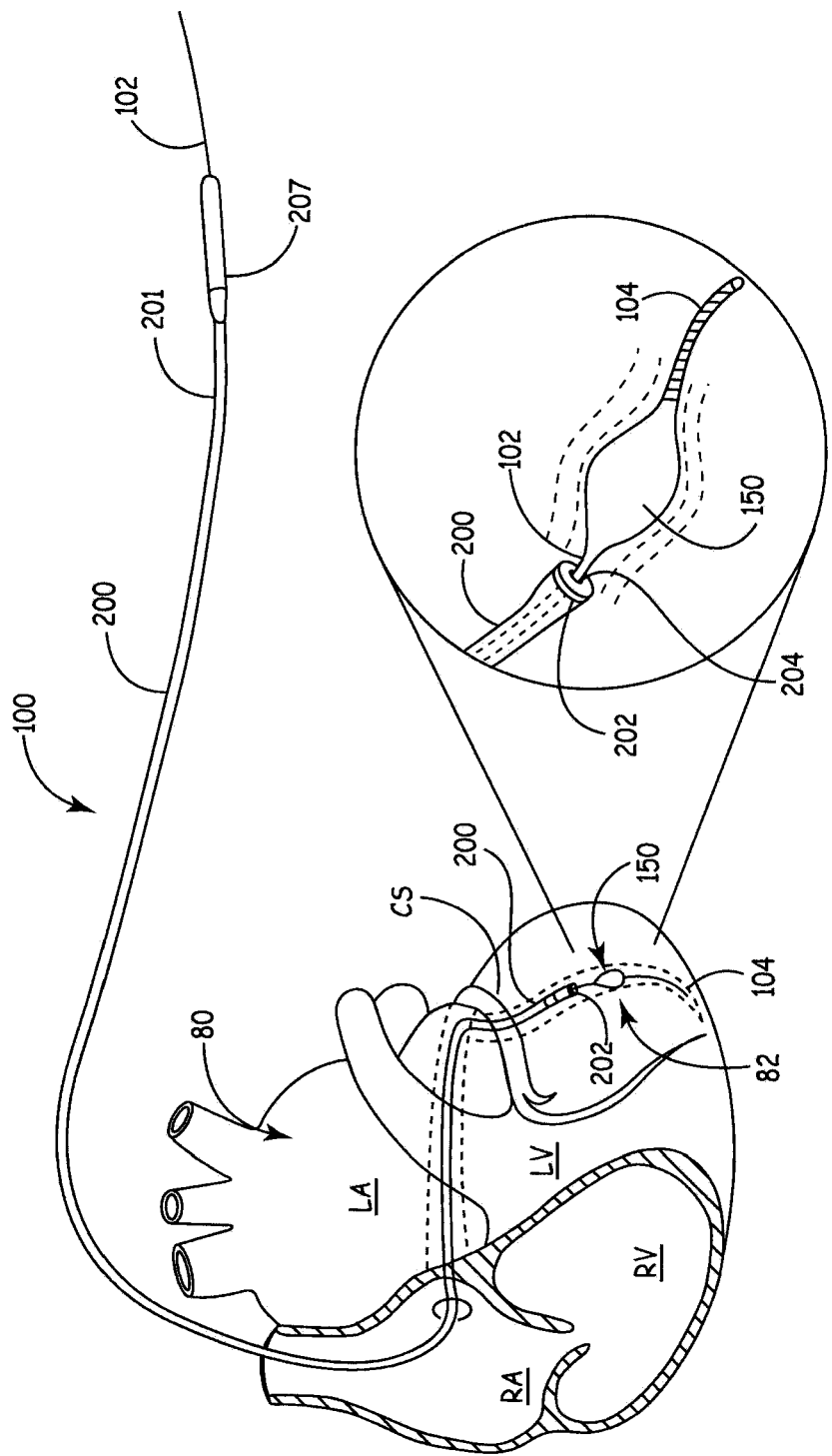
FIG. 1A is an environmental view of the lead delivery device of FIG. 1, shown in a second aspect.
FIG. 1B is an enlarged detail of the lead delivery device of FIG. 1B.
Figure 2:
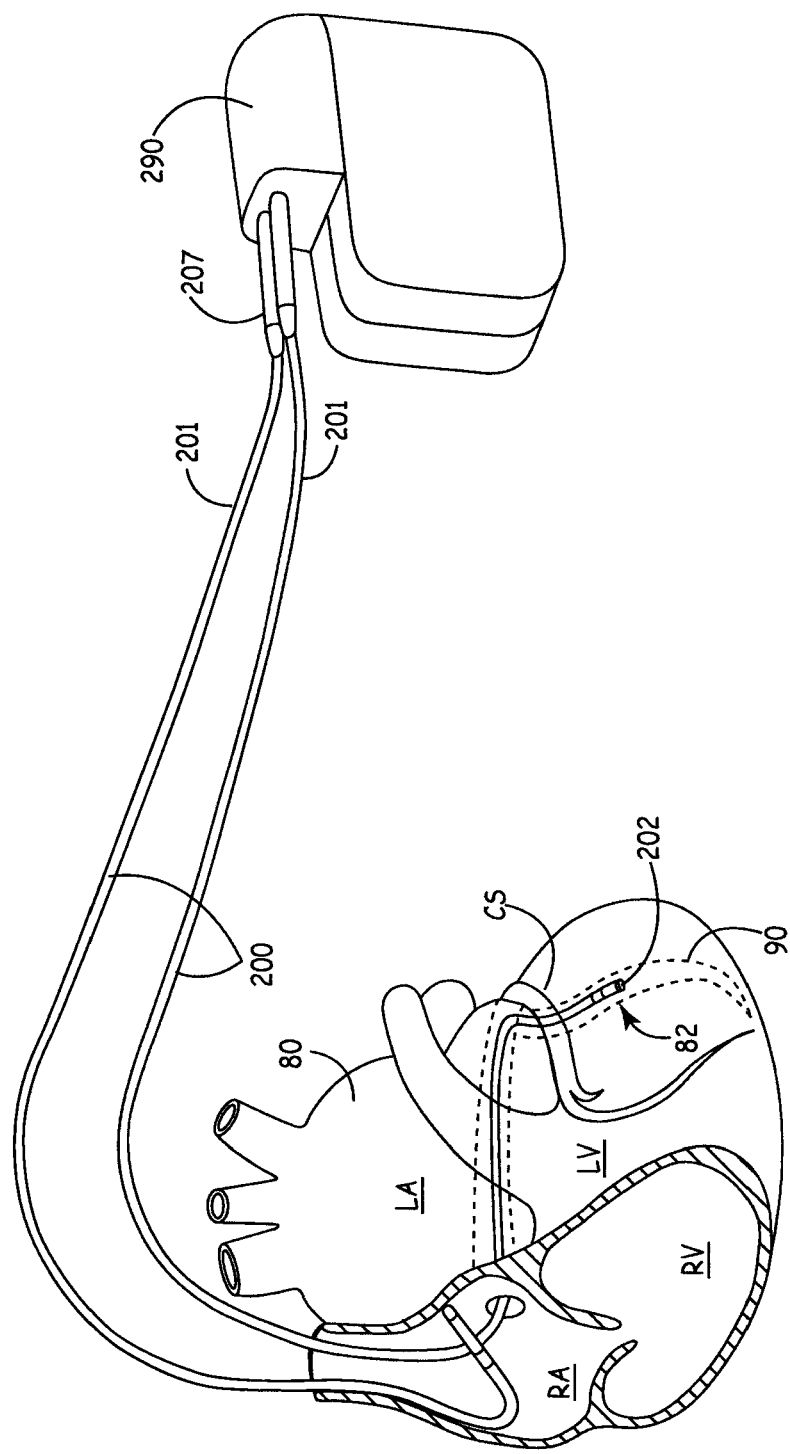
FIG. 2 is a perspective environmental view of the cardiac device with the lead implanted after the lead delivery device of FIG. 1B is removed.

An exemplary lead delivery device 100 according to the present teachings is illustrated during lead delivery of an electrically conductive lead 200 in FIGS. 1, 1A and 1B. An implanted lead 200 is shown in FIG. 2, after the lead delivery device 100 is removed. The lead 200 can be cannulated having an internal bore or lumen 204, a proximal portion 201, and a distal portion 202. The proximal portion 201 can be coupled with a connector pin 207 to a connector block of a cardiac device 290, with which the lead 200 is in electrical communication. A catheter 250 having a proximal end 252 and a distal end 254 can be used to insert the lead delivery device initially through heart tissue 80, as shown in FIG. 1.

The lead delivery device 100 can include a guidewire 102 entering a proximal end 252 of the catheter 250 and exiting through a distal end 254 of the catheter 250 as shown in FIG. 1. The guidewire 102 can be solid or cannulated with a bore 103, as shown in FIG. 12. The guidewire 102 can include a distal portion 104 terminating in a tip 106. The distal portion 104 can be flexible for ease in guiding the guidewire 102 through tortuous blood vessels to a target site 82, such as a branching vein branching off the coronary sinus or other main blood vessel. The lead delivery device 100 can include a fixator 150 coupled to the guidewire 102. The fixator 150 can assume an expanded or deployed configuration for anchoring the guidewire 102 near a target site 82 during lead delivery and implantation, as shown in FIGS. 3, and 5-11, illustrating various fixator aspects. Referring to FIG. 1, the catheter 250 can be removed by retracting the catheter 250 from heart tissue 80 after the lead delivery device is anchored at the target site 82. No slitting of the catheter 250 is required for removal of the catheter 250. After the catheter 250 is removed, the lead 200 can be guided over the guidewire 102 to the target site 82, as discussed further below.

The fixator 150 can be returned to a compact or undeployed configuration, such as the configuration illustrated in FIG. 4, for retracting and removing the guidewire 102 after lead delivery and implantation. The maximum dimension, diameter or width of the fixator 150 in the expanded configuration is denoted as L1 and in the contracted configuration as L2, as illustrated in FIGS. 3 and 4 for a fixator in the form of a balloon.

FIGS. 5-11 illustrate various fixators 150 in their expanded configuration showing the maximum dimension L1 for each fixator 150. The dimension L1 is selected to achieve a fixation force within a blood vessel of an amount that allows the guidewire 102 to be pulled in tension without being dislodged from the blood vessel while the lead is pushed over the guidewire 102, as discussed below. The fixation force F can be equal to or greater than about 2.24 N, or about 0.5 lbs, for achieving sufficient fixation within the blood vessel wall. The fixation force F can generally be in the range of about 0.89 to 4.45 N (or 0.2 to 1.0 lbs), depending on various factors, including the geometry of the branching vessel. The deployed width or dimension L1 corresponding to this fixation force F can be 5 mm, while the undeployed width or dimension L2 can be maintained to equal to or less than about 0.019 inches, or about 0.483 mm, to allow easy passage through commercially available leads, such as those used with medical devices available from Medtronic, Inc., of Minneapolis, Minn.

Figure 13:
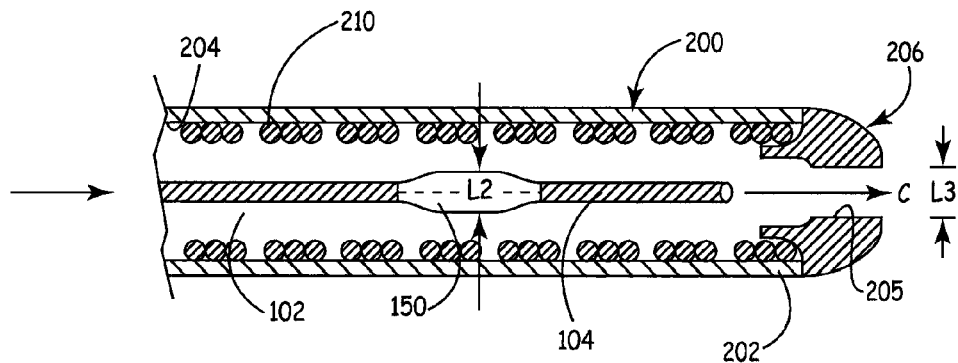
FIG. 13 is a sectional view of a lead delivery device according to the present teachings with a fixator in a compact configuration inside a lead.
Figure 14:
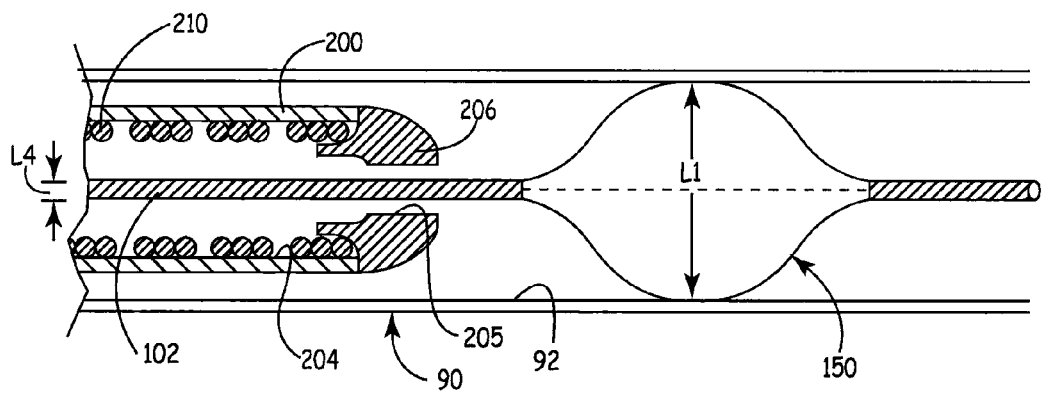
FIG. 14 is the lead delivery device of FIG. 13, shown with the fixator in an expanded configuration outside the lead.
Figure 15:
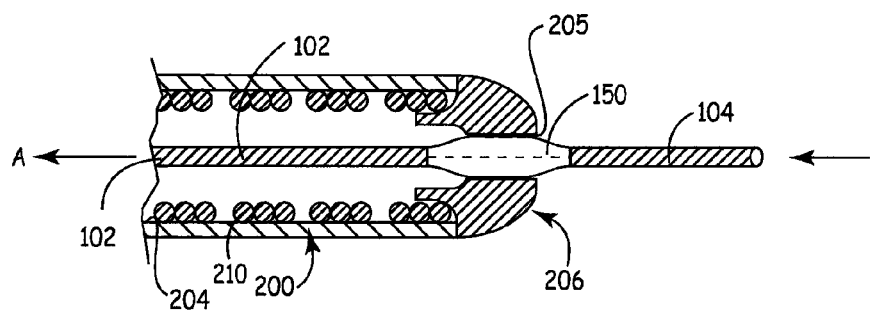
FIG. 15 is the lead delivery device of FIG. 13, shown with the fixator partially retracted inside the lead.

Referring to FIGS. 13-15, the distal portion 202 of an electrical lead 200 is illustrated in connection with a guidewire 102 having a width L4 and a fixator 150 having an undeployed width L2. The lead 200 is conductive and can deliver therapy in the form of electric energy at the target site 82. In one aspect, the lead 200 can also sense and relay information about electrical activity from the heart tissue 80 or target site 82 back to the cardiac device 290. The lead 200 can have an internal bore or lumen 204, an internal coil or other conductive element 210 and a tip portion 206 that can be an electrode tip with or without a seal. The tip portion 206 can define a distal opening 205 with width L3. In one aspect, the tip portion 206 can include a seal with flexible flaps, not shown. The guidewire width L4 can be about 0.346 mm (or about 0.014 inches) for providing steerability, stiffness and sufficient support for lead delivery over the guidewire 102.

Figure 16:
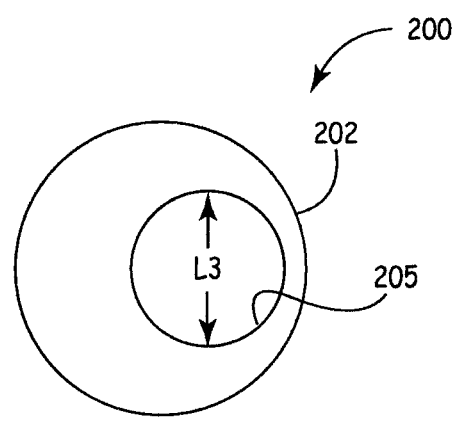
FIG. 16 is an end view of a distal end of an electrical lead with an offset distal opening.

The compact width L2 of the fixator 150 can be equal to or less than the width L3 of the distal opening 205, such that the fixator 150 can be pushed through the distal opening 205 in the direction C, as shown in FIG. 13. In one aspect the distal opening 205 can be offset relative to a central longitudinal axis of the lead 200, as shown in FIG. 16. The fixator 150 can be deployed to the expanded configuration within the blood vessel 90 such that the expanded width L1 of the fixator 150 can press against the internal lumen 92 of the blood vessel 90 with a holding force F, as discussed above, for temporarily anchoring the guidewire 102 into the blood vessel 90, as shown in FIG. 14.

Figure 5:
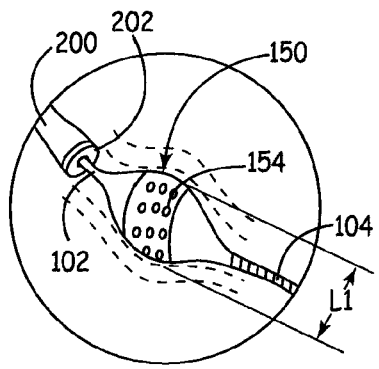
FIGS. 5-11 illustrate various fixators for a lead delivery device according to the present teachings.
Figure 7:
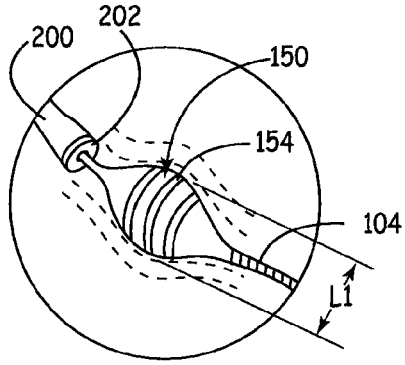

Various fixators 150 can be used to temporarily and removably anchor the guidewire 102 in the lumen 92 of a blood vessel 90. Referring to FIGS. 3 and 4, the fixator 150 can be a balloon having first and second ends 111, 113 attached to the guidewire 102. The balloon can be inflated, for example, with a gas or fluid, including a gel or other liquid, provided by a syringe through a valve 110 at a proximal end of the guidewire 102. In another aspect, a luer lock inflation port 120 can be coupled to the guidewire 102 for deploying the balloon. The balloon can be made from a polyblend material which is heated and stretched, placed around the guidewire 102 and bonded at first and second ends 111, 113 of the balloon onto the guidewire 102 with small amounts of cyanoacrylate adhesive, for example. A radio-opaque marker 108 in the form of a band can be placed adjacent the second (proximal) end 113 of the balloon for visualization during guided navigation. The radio-opaque marker 108 can also be in the form of a radio-opaque balloon coating or radio-opaque fluid filling the balloon. In another aspect, the balloon-type fixator 150 can include an etched fixation surface with etched surface fixation formations 154 in the form of bumps, rings, etc., as illustrated in FIGS. 5 and 7. In another aspect, the fixator 150 can be a balloon with spiral or helical or otherwise curved configuration for maintaining a percentage of blood flow through the blood vessel 90 and aiding fixation in tortuous anatomy.

Figure 9:
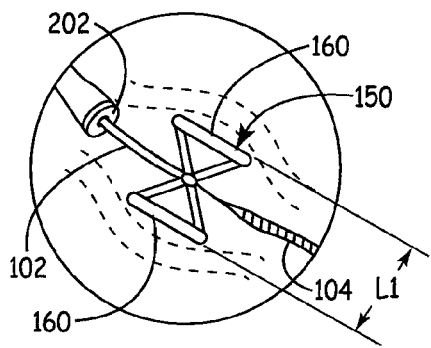
Figure 10:
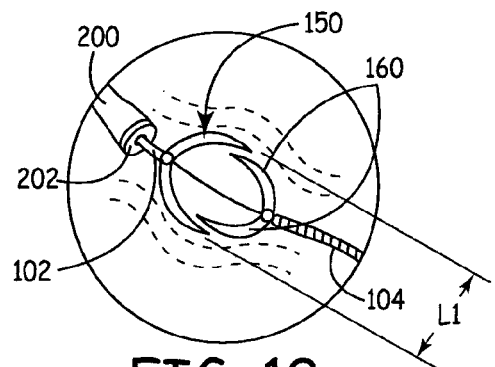
Figure 11:
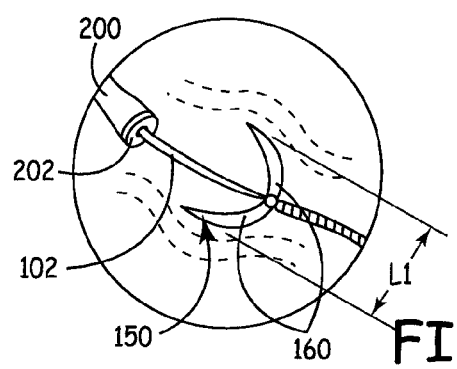
Figure 11A:
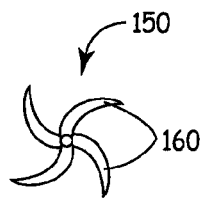
FIG. 11A is a top view of the fixator of FIG. 11.
Figure 12:
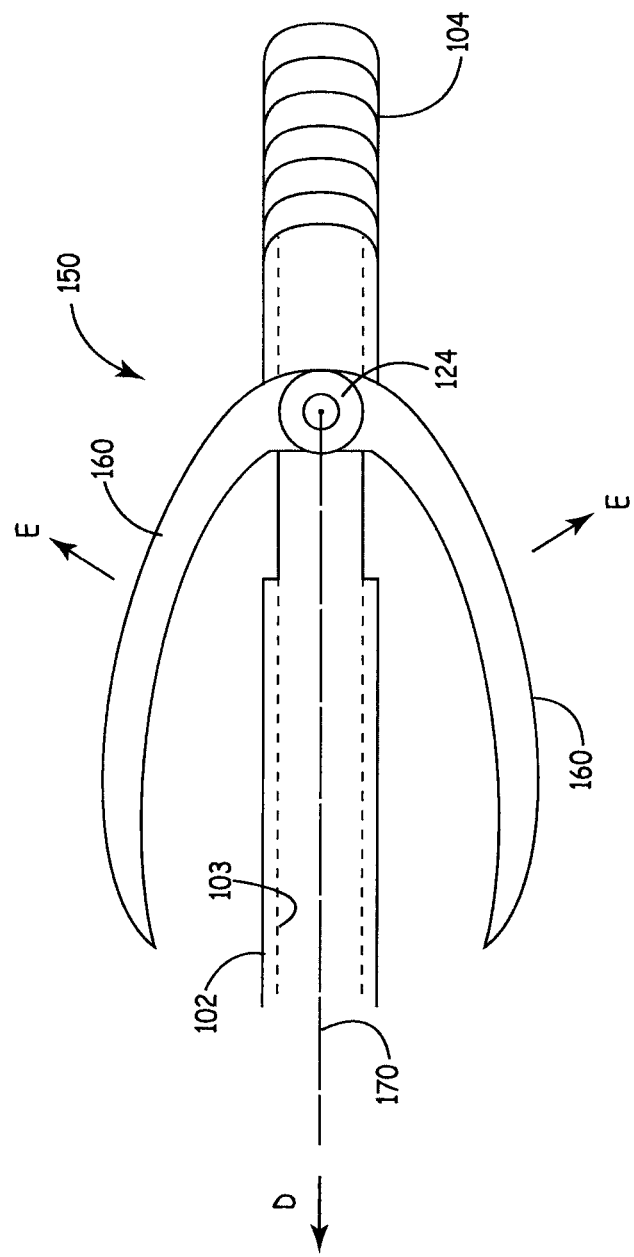
FIG. 12 is a side view of the fixator of FIG. 11, illustrating a deployment mechanism.

Referring to FIGS. 9-12, the fixator 150 can also be in the form of a mechanical anchor with deployable straight wings 160, as shown in FIG. 9, or curved wings 160, as shown in FIG. 10, or a pinwheel-type fixator 150, as shown in FIGS. 11 and 11A. The mechanical anchor 150 can be deployed with a longitudinal actuator 170 in the form of a wire or string or other elongated member passing through the bore 103 of a cannulated guidewire 102. Referring to FIG. 12, for example, the anchor wings 160 can pivot about a pivot pin 124 connected to the actuator 170 and can be deployed to the expanded position in the direction of arrows E by pulling the actuator 170 in the direction of arrow D. In other aspects, the fixator 150 can be in the form of a superelastic wire, such as nitinol, and can be pre-shaped to expand to an anchorable configuration within the blood vessel 90.

Figure 6:
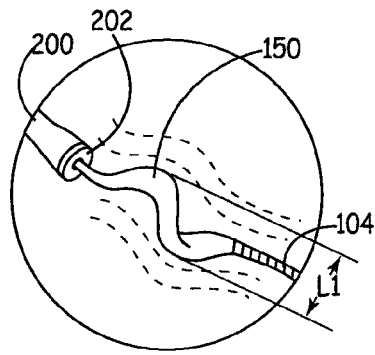
Figure 8:
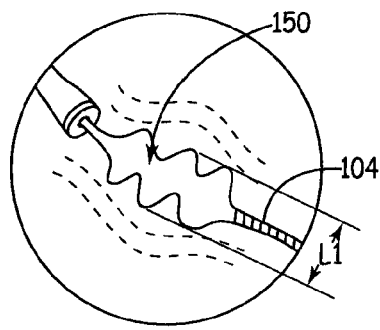

In another aspect, fixators 150 including polymer lobes or superelastic or memory-shape wire can be used. Further, the dimensions of the fixator 150, including the expanded width L1 and the compact width L2 can be selected to match the range of most common vessel sizes. The expanded shape of the fixator 150 can be selected to increase the contact area with the blood vessel and or provide multiple contact surfaces for increasing holding force and stability, as shown in FIGS. 6, 8, and 10, for example. The expanded shape can have a symmetric profile, as shown in FIG. 9, for example, or a non-symmetric profile, as shown in FIG. 6, for example. In other aspects, the expanded shape can have an asymmetric profile for anchoring unidirectionally rather than bi-directionally.

Figure 23:
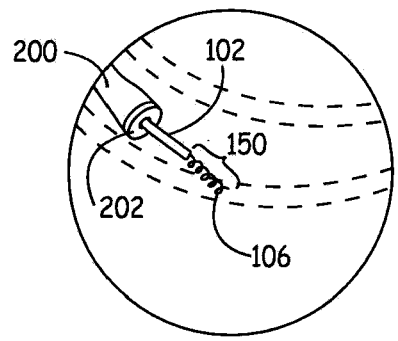
FIG. 23 illustrates an exemplary fixator for a lead delivery device according to the present teachings.

Further exemplary fixators 150 are illustrated in FIGS. 23-34. The fixator 150 can be in the form of a mechanical helix that temporarily secures the guidewire 102 to a vessel wall, as shown in FIG. 23. The mechanical helix may be formed of a metal or polymer material attached to the distal portion 106 of the guidewire 102. The mechanical helix may be permanently attached to the distal end 104 of the guidewire 102, or may selectively retract within, or extend from, an inner lumen of the guidewire 102. The mechanical helix may share a common axis with the guidewire 102 as shown. Alternatively, the axis of the mechanical helix may be movable to be angled (for example, approximately 90°) with respect to the axis of the guidewire.

Figure 24:
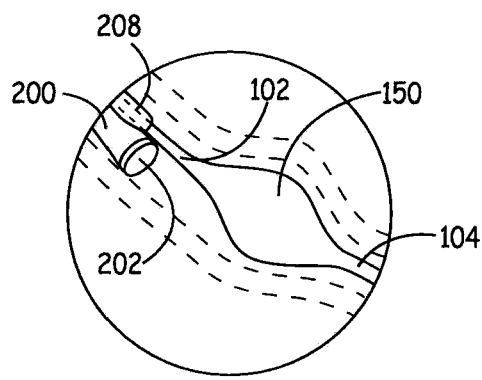
FIG. 24 illustrates an exemplary fixator for a lead delivery device according to the present teachings.
Figure 25:
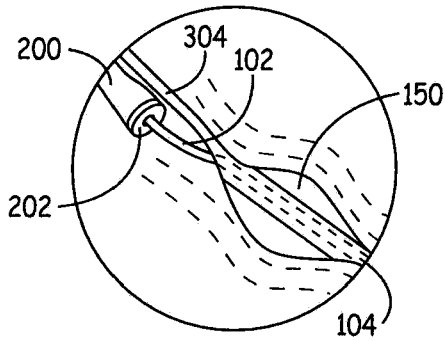
FIG. 25 illustrates an exemplary fixator for a lead delivery device according to the present teachings.

As illustrated in FIG. 24, a balloon fixator 150 may be utilized with a lead 200 that does not include an inner lumen. The lumenless lead 200 may be guided along the guidewire 102 by guiding passage 208 or similar connection that slidably couples lead 200 with guidewire 102. Additionally, as discussed more fully below, fixator 150 may take the form of a balloon attached to a fixator catheter 304 through which the guidewire 102 passes.

Figure 26:
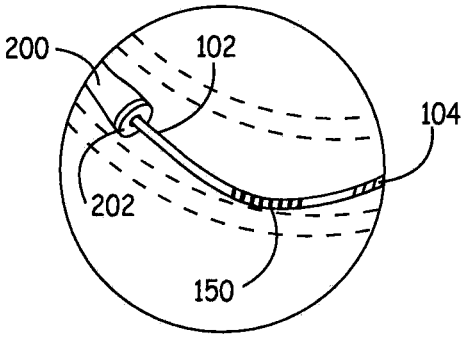
FIG. 26 illustrates an exemplary fixator for a lead delivery device according to the present teachings.
Figure 27:
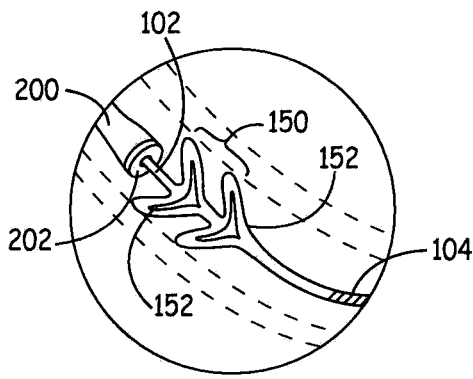
FIG. 27 illustrates an exemplary fixator for a lead delivery device according to the present teachings.

Fixator 150 may take the form of a magnetic fixator that temporarily secures the guidewire 102 to a vessel wall, as shown in FIG. 26. The magnetic fixator 150 will respond to an external magnetic field or magnetic field outside of the patient that secures the guidewire 102 against a vessel wall. Upon removal of the magnetic field, the magnetic fixator 150 may be freely moved within the vessel. FIG. 27 illustrates yet another exemplary fixator 150 that comprises at least one expandable lobe 152. The expandable lobe 152 may have various shapes and be made of a polymer, metal or similar material. The lobe 152 may be deployed to secure fixator 150 and guidewire 102 within a vessel, and then collapsed or otherwise released from vessel wall for removal.

Figure 28:
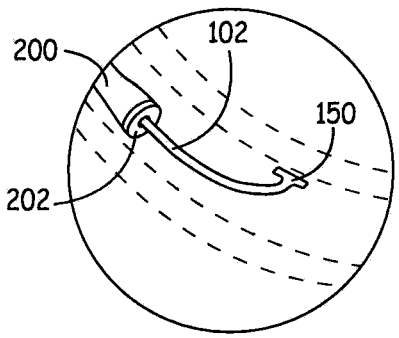
FIG. 28 illustrates an exemplary fixator for a lead delivery device according to the present teachings.
Figure 29:
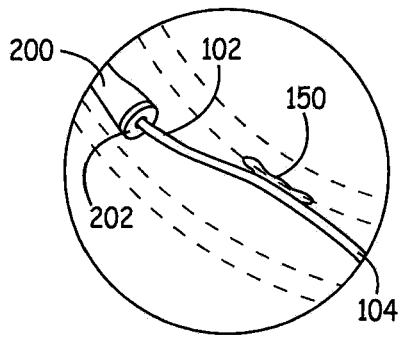
FIG. 29 illustrates an exemplary fixator for a lead delivery device according to the present teachings.

FIG. 28 illustrates an exemplary fixator 150 that takes the form of a guidewire 102 with an inner lumen terminating in a suction tip through which a suction force may be exerted. The suction force may be applied to secure the fixator 150 to a vessel wall and, upon removal of the suction force, the guidewire 102 will be released from attachment to the vessel wall. Alternatively, an adhesive may be used as the fixator 150 for securing the guidewire 102 to a vessel wall, as shown in FIG. 29. The adhesive may be a biocompatible adhesive, a bio-gel, or other form of self-dissolving adhesive that temporarily secures the guidewire 102 to a vessel wall during a surgical procedure. The adhesive may provide a retention force that permits navigation of the lead 200 during a procedure, but that allows for removal of the guidewire 102 upon exertion of a force on the guidewire 102 in excess of that expected during guidance of the lead 200. In this manner, guidewire 102 may be removed from vessel after completion of the procedure.

Figure 30:
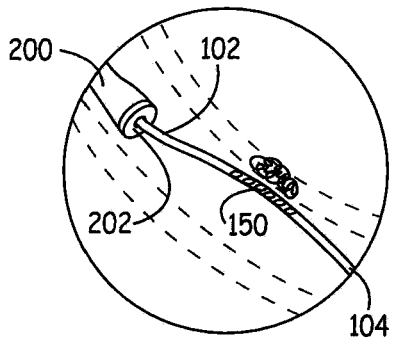
FIG. 30 illustrates an exemplary fixator for a lead delivery device according to the present teachings.

The fixator 150 may also take the form of a temperature controllable portion of the guidewire 102 that may be temporarily adhered to a vessel wall through heating or freezing, as illustrated in FIG. 30. In this example, the guidewire 102 may include an inner lumen that may be filled with a liquid at a temperature that will cause freezing of the temperature controllable portion of the guidewire 102, which will adhere to the vessel wall. Alternatively, the temperature controllable portion of the guidewire 102 may be heated, e.g., by electrical energy, to cause adhesion between the vessel wall and guidewire 102. Upon removal of the heating or freezing source, the fixator 150 will release from the vessel wall.

Figure 31:
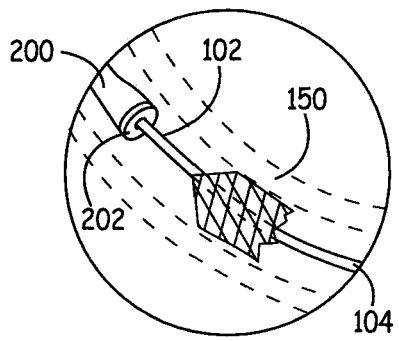
FIG. 31 illustrates an exemplary fixator for a lead delivery device according to the present teachings.
Figure 32:
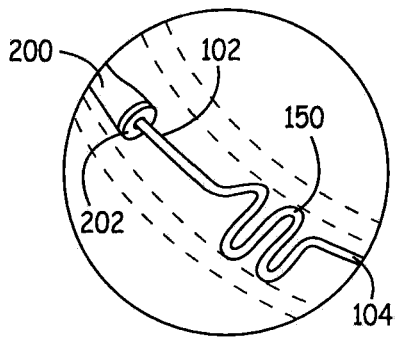
FIG. 32 illustrates an exemplary fixator for a lead delivery device according to the present teachings.

FIG. 31 illustrates yet another form of fixator 150. In this example, fixator 150 takes the form of an expandable mesh cage or stent that may be selectively expanded and contracted. Additionally, the mesh cage or stent may be made of a dissolvable material and released from attachment with guidewire 102 after completion of a procedure. In various embodiments, a permanent mesh cage or stent may be attached to the guidewire 102 by means of a dissolvable material such that the mesh cage or stent is released from attachment with guidewire 102 after completion of a procedure to remain in the blood vessel. Alternatively, the fixator 150 may take the form of a portion of the guidewire 102 that may be selectively formed into an expanded shape, as shown in FIG. 32. As shown in FIG. 32, a portion of the guidewire 102 at the distal end 104 may be activated to form an anchor shape, such as a corkscrew as shown. The anchor shape of the guidewire 102 may be activated electrically, mechanically or a combination of both. For example, electrically activated polymers, metals or other materials may be used to form the fixator 150 such that, when an electric current is provided thereto, the fixator 150 takes an expanded form. Other fixator 150 activation methods are described more fully below.

Figure 33:
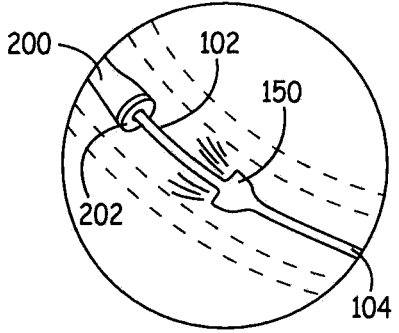
FIG. 33 illustrates an exemplary fixator for a lead delivery device according to the present teachings.
Figure 34:
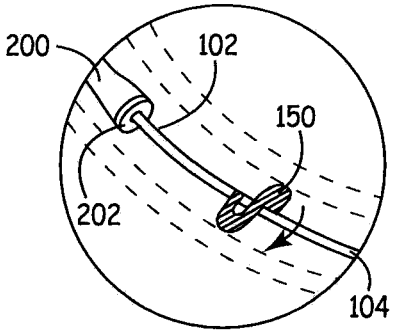
FIG. 34 illustrates an exemplary fixator for a lead delivery device according to the present teachings.

Referring now to FIGS. 33-34, a propelled guidewire 102 with a propulsion element that acts as a fixator 150 may be utilized. The propulsion force exerted by the guidewire 102 in the forward direction will counter the force exerted by an operating physician in the backward direction when guiding the lead 200 into the target area. In this example, the fixator 150 may take the form of propulsion jets (as shown in FIG. 33), a propeller (as shown in FIG. 34) or other propulsion source.

As discussed above, deployment of the fixator 150 and anchoring can occur after the cannulation of the coronary sinus CS with the catheter 250 and after sub-selection of a side branch with the guidewire 102. Further, fixation of the guidewire 102 by the expandable fixator 150 can be maintained during lead delivery and terminated after the lead 200 is delivered to the target vessel at the target site 82. At the discretion of the operating physician, fixation and release can occur multiple times during the medical procedure. Damage to the lead 200 during fixation can be avoided because fixator expansion and fixation occurs outside the lead 200.

Figure 35:
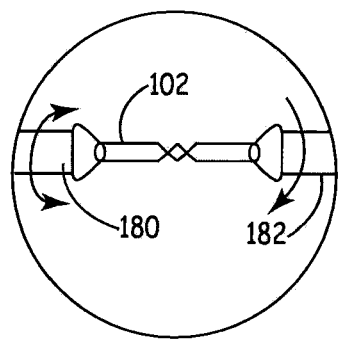
FIG. 35 illustrates an exemplary device for expanding a fixator for a lead delivery device according to the present teachings.
Figure 37:
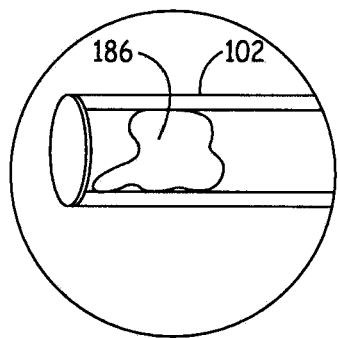
FIG. 37 illustrates an exemplary device for expanding a fixator for a lead delivery device according to the present teachings.
Figure 36:
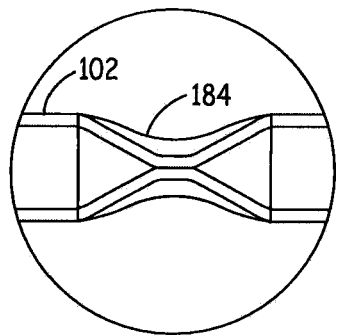
FIG. 36 illustrates an exemplary device for expanding a fixator for a lead delivery device according to the present teachings.
Figure 38:
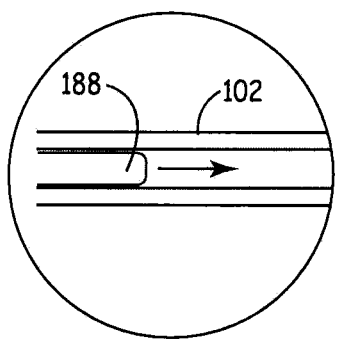
FIG. 38 illustrates an exemplary device for expanding a fixator for a lead delivery device according to the present teachings.

Various devices and methods of deploying the fixator 150 may be utilized. An example of such a fixator deployment device is shown in FIG. 35, with which the inner lumen of guidewire 102 (or fixator catheter 304 discussed more fully below) may be twisted closed through the use of removable handles or torque tools 180 and 182. In this manner, for example, a balloon or other receptacle may be filled with pressurized fluid to enter and maintain the expanded condition. Alternatively, a collapsible sleeve 184 may be secured on the guidewire 102 to close the inner lumen, as shown in FIG. 36. The collapsible sleeve 184 and guidewire 102 may be isodiametric, i.e., having the same outer diameter. Additionally, an adhesive or high viscosity paste or gel 186 may be inserted into and seal the inner lumen, as seen in FIG. 37. Other methods of sealing the inner lumen of the guidewire 102 include utilizing a clamp or other crimping device to close and seal the inner lumen to maintain the fixator 150 in the expanded condition. In various embodiments, as FIG. 38 illustrates, a push rod or piston 188 may be slidably engaged with the inner lumen and used to actuate the fixator 150 between the expanded and collapsed state. In each of the above examples, each of the deployment systems may be made to be isodiametric with the guidewire 102 such that they may be deployed through the distal opening 205 of the lead 200.

Figure 39:
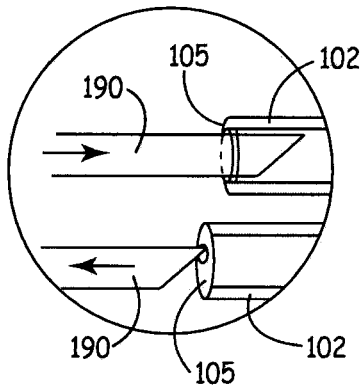
FIG. 39 illustrates an exemplary device for expanding a fixator for a lead delivery device according to the present teachings.

In other embodiments, as shown in FIG. 39, for example, the proximate end 105 of guidewire 102 may be formed of a self-sealing polymer or similar material such that a needle 190 may be inserted into the inner lumen of the guidewire 102 to introduce a pressurized fluid into the inner lumen to expand the fixator 150. After expansion of the fixator 150, the needle 190 may be removed from the guidewire 102 and the proximate end 105 will automatically seal the inner lumen, thus maintaining the pressure within the inner lumen and the fixator 150 in the expanded condition. As discussed more fully below, a fixator catheter 304 may be utilized similarly to the guidewire 102 in the above examples. Furthermore, in each of the above examples, the guidewire 102 or fixator catheter 304 may be cut between the closed portion of the inner lumen and the fixator 150 to release the pressure and collapse the fixator 150.

It should be appreciated, that according to the present teachings the lead delivery device 100 with either a balloon or mechanical fixator 150 is configured and designed to function as a wedge or anchoring device for temporarily anchoring the guidewire 102 during the implantation of the electrical lead 200.

Referring to FIGS. 1-2, and 13-15, the cannulated catheter 250 can be inserted through heart tissue 80 into a coronary sinus CS, cardiac great vein or other main vessel stopping short of a target site 82 that is located in a sub-selected acute branching vessel 90. The guidewire 102 with the fixator 150 in the undeployed compact configuration can be inserted through the catheter 250, advanced past the distal end 254 of the catheter 250 through a main vessel to the target site 82 in the branching vessel 90, as shown in FIG. 1. The fixator 150 can then be deployed and become anchored in the lumen 92 of the branching vessel 90 with a holding force F, as discussed above. The catheter 250 can then be retracted and completely removed with no slitting procedure. The lead 200 can be guided over the anchored guidewire 102 until the distal portion 202 of the lead 200 reaches the target site 82, as shown in FIG. 1B. The lead 200 can be advanced by keeping the guidewire 102 in tension while pushing the lead 200 in the direction of the fixator 150. When the distal portion 202 of the lead 200 reaches the target site 82, the fixator 150 can be returned to its undeployed compact configuration and be retracted through the lumen 204 of the lead 200, as shown in FIG. 15. The lead 200 can remain installed in the target site 82, as shown in FIG. 2, or advanced more distally in the branching vessel 90 beyond the original target site 82 after the removal of the guidewire 102.

It will be appreciated that, in other aspects, the catheter 250 may be retained during the entire lead delivery procedure, such that the lead is inserted through the catheter 250 and over the guidewire 102, but in such cases slitting of the catheter 250 may not be avoided after lead implantation. In further aspects, the guidewire 102 and the lead 200 can be inserted through the catheter 250 in any order, i.e., guidewire 102 first, or lead 200 first or at the same time. In all aspects, however, the guidewire 102 can first be advanced to the target site 82 of a branching vessel 90 and the fixator 150 be deployed at the target site 82. Only then the distal portion 202 of the lead 200 is advanced to the target site 82 by pushing the lead 200 over the guidewire 102 toward the target site 82, while the guidewire 102 remains fixed. Specifically, the lead 200 can be advanced to the target site 82 in a climbing-like or zip line-like manner by pulling and tensioning the guidewire 102 while the guidewire 102 remains anchored with the deployed fixator 150 at the target site 82.

Figure 17:
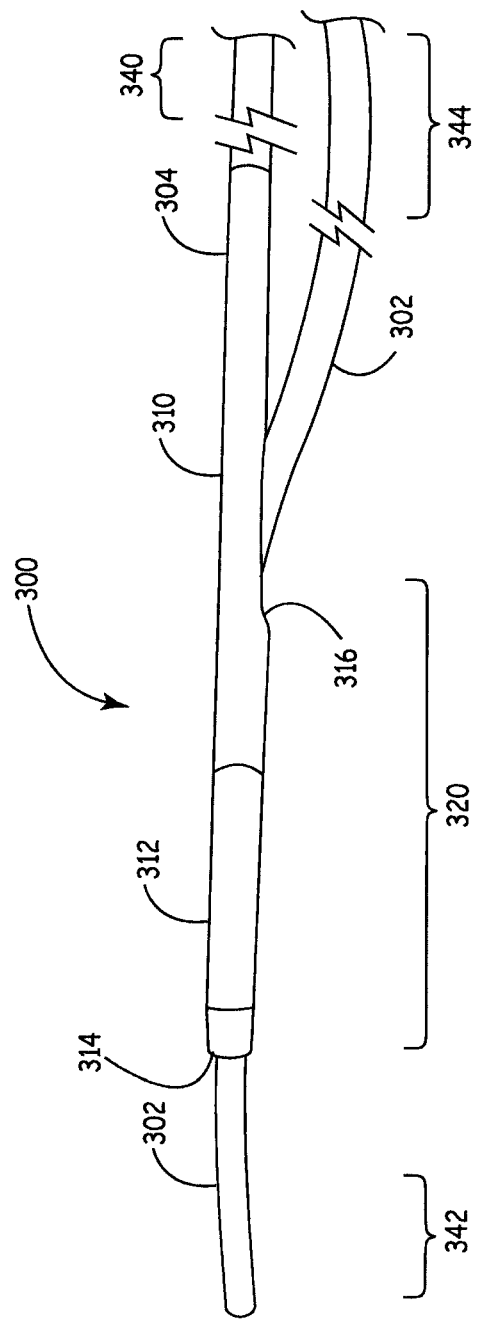
FIG. 17 is a plan view of a lead delivery device having a fixator according to the present teachings, the lead delivery device shown with the fixator in a compact configuration.

Referring now to FIG. 17, a lead delivery device 300 according to some embodiments of the present disclosure is illustrated. Lead delivery device 300 comprises a guidewire 302 and fixator catheter 304. Guidewire 302 may comprise a solid wire (as illustrated) or be cannulated, and includes proximal portion 344 and distal portion 342. The fixator catheter 304 is a cannulated catheter comprising a tubular body 310 with a distal portion 320 and proximal portion 340. A fixator 312 is secured on the distal end 320 of fixator catheter 304. In FIGS. 17-22, fixator 312 comprises an inflatable balloon, although any other form of fixator may be utilized, as described above.

Guidewire 302 passes through fixator catheter 304 such that the guidewire 302 is encased within the tubular body 310 in at least a portion of the distal portion 320 of the fixator catheter 304. In the illustrated embodiments, this is accomplished by passing the distal portion 342 of the guidewire 302 through the body opening 316 of fixator catheter 304 such that it extends through the distal opening 314. In this manner, the guidewire 302 and fixator catheter 304 are in communication at their distal portions 342, 320, while being separate at their proximal portions 344, 340.

Figure 18:
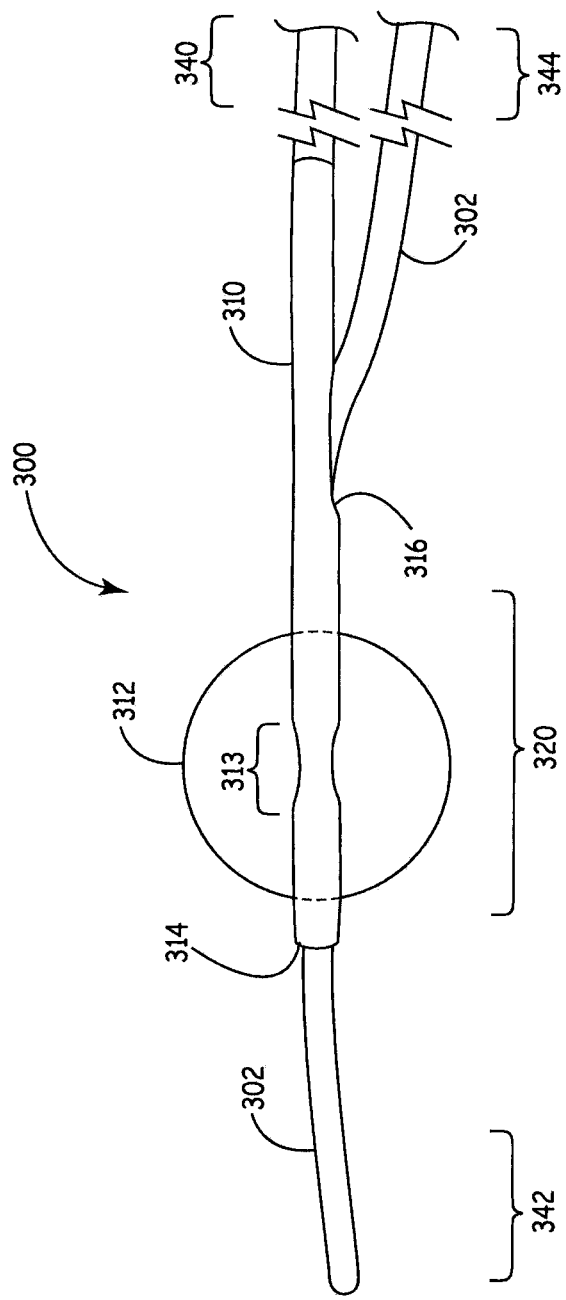
FIG. 18 is a plan view of a lead delivery device having a fixator according to the present teachings, the lead delivery device shown with the fixator in an expanded configuration.

Referring now to FIG. 18, lead delivery device 300 is shown in the condition where fixator 312 is expanded. In the illustration, fixator 312 comprises an inflatable balloon that may be expanded by a gas or fluid, as described more fully above. In some embodiments, the tubular body 310 of the fixator catheter 304 includes a lumen (not shown) that is in communication with the inflatable balloon 312 and proximal end 340. By providing a pressurized gas or fluid to the balloon 312, the fixator 312 is expanded to the expanded configuration. In the expanded configuration, the pressure inside balloon 312 will exert a force on a compressible or collapsible portion 313 of tubular body 310. In the illustrated embodiment, the compressible portion 313 is a portion of the lumen of the fixator catheter within the inflatable balloon, however, the compressible portion 313 may comprise a lumen of the balloon itself or other arrangement. The force exerted by inflatable balloon 312 on portion 313 of tubular body 310 will cause that portion 313 to compress guidewire 302 such that guidewire 302 is secured to fixator catheter 304. Portion 313 may be formed by providing a thinner wall in portion 313 than is utilized in the remainder of tubular body 310. Alternatively, portion 313 may be formed of a different material than that used to form the rest of tubular body 310, or any other alternative structure may be utilized (such as, adding a constrictive device or other securing mechanism). While the illustration in FIG. 18 shows an inflatable balloon 312 and a compressible or contract portion 313 of tubular body 310 to secure the guidewire 302 to fixator catheter 304, alternative structures and fixators may be substituted such that the guidewire 302 and fixator catheter 304 are secured together in the expanded configuration, while remaining independently movable in the compact configuration.

As alluded to above, the guidewire 302 may be secured to the fixator catheter 304 by an apparatus other than the collapsible portion 313 of tubular body 310. For example, if the mechanical helix fixator 150 illustrated in FIG. 23 is utilized, the fixator catheter 304 may be forced to kink or otherwise secure the guidewire 302 during deployment and attachment of the mechanical helix to the vessel wall. With the magnetic fixator 150 embodiment illustrated in FIG. 26, an external magnetic force may act on a portion of the fixator catheter 304 to secure the guidewire 302 thereto. With the fixators 150 illustrated in FIGS. 27, 31 and 32, for example, the force utilized to expand the fixator 150 may be utilized to compress and anchor the guidewire 302 within the fixator catheter 304, similarly to that described above with respect to the balloon fixator catheter. A fixator catheter 304 with the suction tip fixator 150 as illustrated in FIG. 28 may include an additional suction port for securing the guidewire 302 within the fixator catheter 304. While each of the alternative securing mechanisms described above are associated with particular fixator 150 embodiments, any combination of fixator 150 and securing mechanisms 150 are within the scope of the present disclosure.

Figure 19:
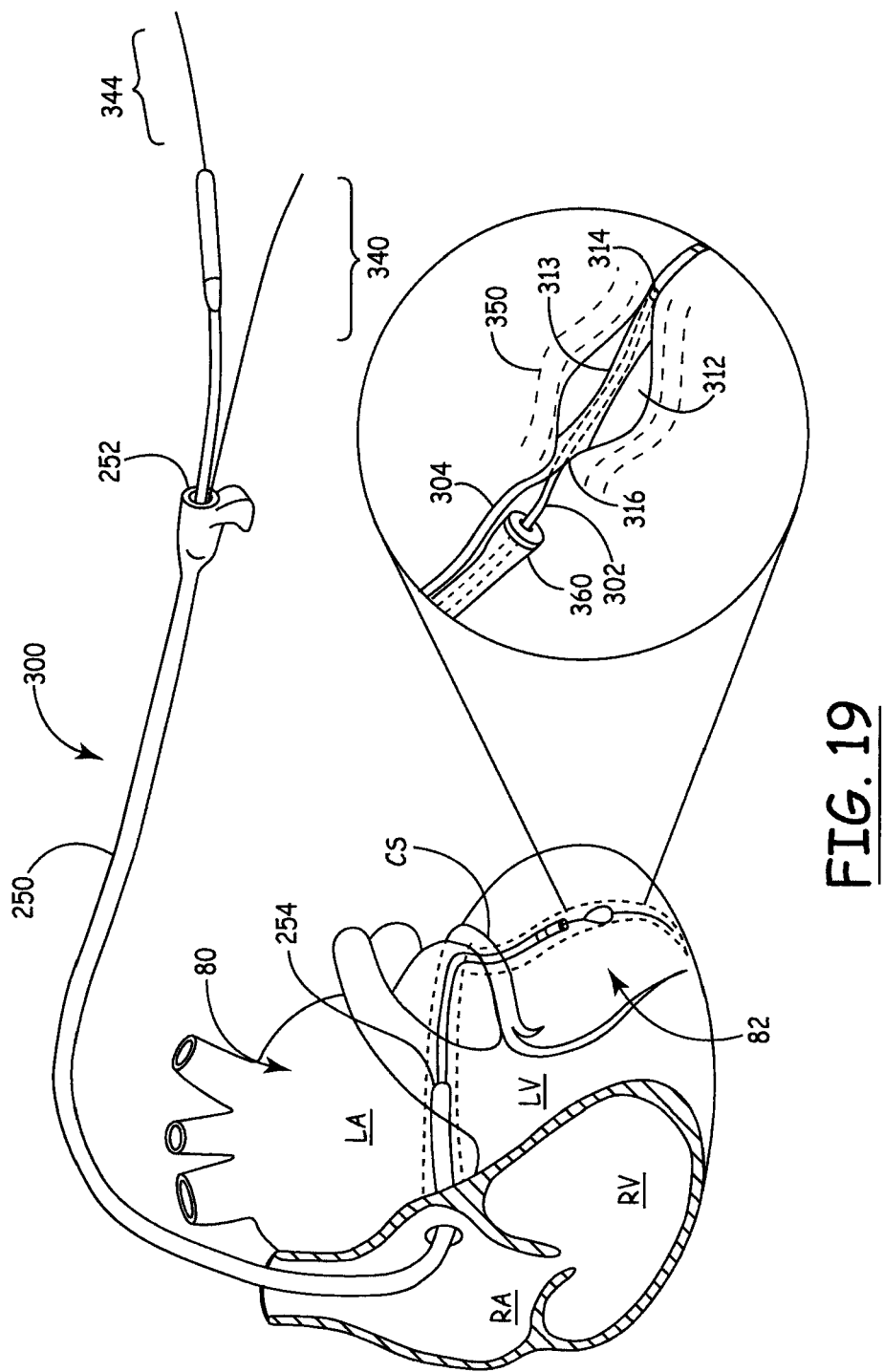
FIG. 19 is an environmental view of a lead delivery device according to various embodiments of the present teachings.
Figure 20:
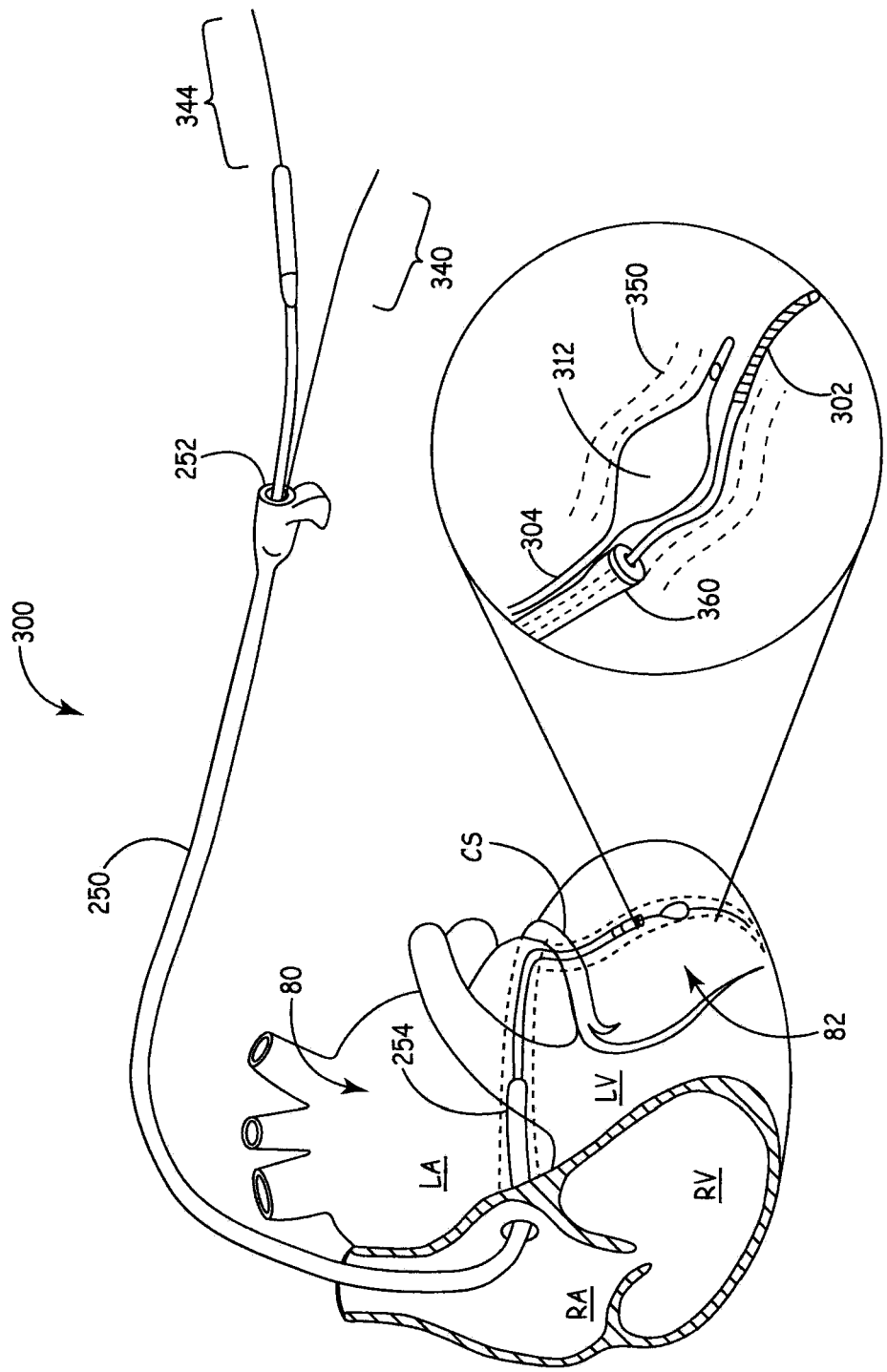
FIG. 20 is an environmental view of a lead delivery device according to various embodiments of the present teachings.

Referring now to FIGS. 19-22, a method for using lead delivery device 300 to implant an implantable electrically conductive lead 360 within a blood vessel 350 is illustrated. Similar to FIG. 1, FIGS. 19-20 show the lead delivery device 300 utilized to implant implantable electrically conductive lead 360 within the coronary sinus CS of heart tissue 80. A delivery catheter 250 having a proximal end 252 and distal end 254 may be utilized to assist in the delivery of guidewire 302 and fixator catheter 304 to a target or desired site 82. The fixator catheter 304, with guidewire 302 passed therein, is inserted through catheter 250 and navigated to a position within the desired site 82. Upon delivery to desired site 82, fixator catheter 304 deploys its fixator 312 to secure guidewire 302 and fixator catheter 304 within blood vessel 350. In the expanded configuration, fixator 312 exerts a force, as described above, upon the wall of blood vessel 350 sufficient to anchor both the guidewire 302 and fixator catheter 304 in the desired site 82 while delivery catheter 250 is removed and/or implantable electrically conductive lead 360 is delivered to desired site 82, e.g., via guidewire 302.

In the illustrations of FIGS. 19 and 20, delivery catheter 250 is shown as being present within the heart tissue 80 during delivery of lead 360. As shown in FIG. 19, in the expanded configuration fixator 312 compresses or collapses portion 313 of fixator catheter 304 such that guidewire 302 is fixedly secured within fixator catheter 304, as described more fully above. Alternatively, as shown in FIG. 20, guidewire 302 may be removed from fixator catheter 304 before fixator 312 is expanded. Fixator 312 may then be expanded to fixedly secure guidewire 302 between fixator 312 and the wall of blood vessel 350. Once guidewire 302 is fixedly secured within blood vessel 350, implantable electrically conductive lead 360 may be delivered to desired site 82 by, e.g., traveling over guidewire 302. With the guidewire 302 secured, the risk of the lead 360 being delivered incorrectly, i.e., outside of desired site 82, due to unintentional movement of guidewire 302 is reduced.

Once lead 360 is delivered to the desired site 82, the fixator 312 may be contracted to a compact configuration (as shown in FIG. 17, for example) and both guidewire 302 and fixator catheter 304 may be removed from desired site 82 and heart tissue 80. In some embodiments, fixator 312 may be utilized to secure lead 360 against blood vessel wall 350 while guidewire 302 is removed (see, e.g., FIG. 22). In this manner, it can be ensured that there is no unanticipated movement of lead 360 from desired site 82 while guidewire 302 is removed from the patient's body.

Figure 21:
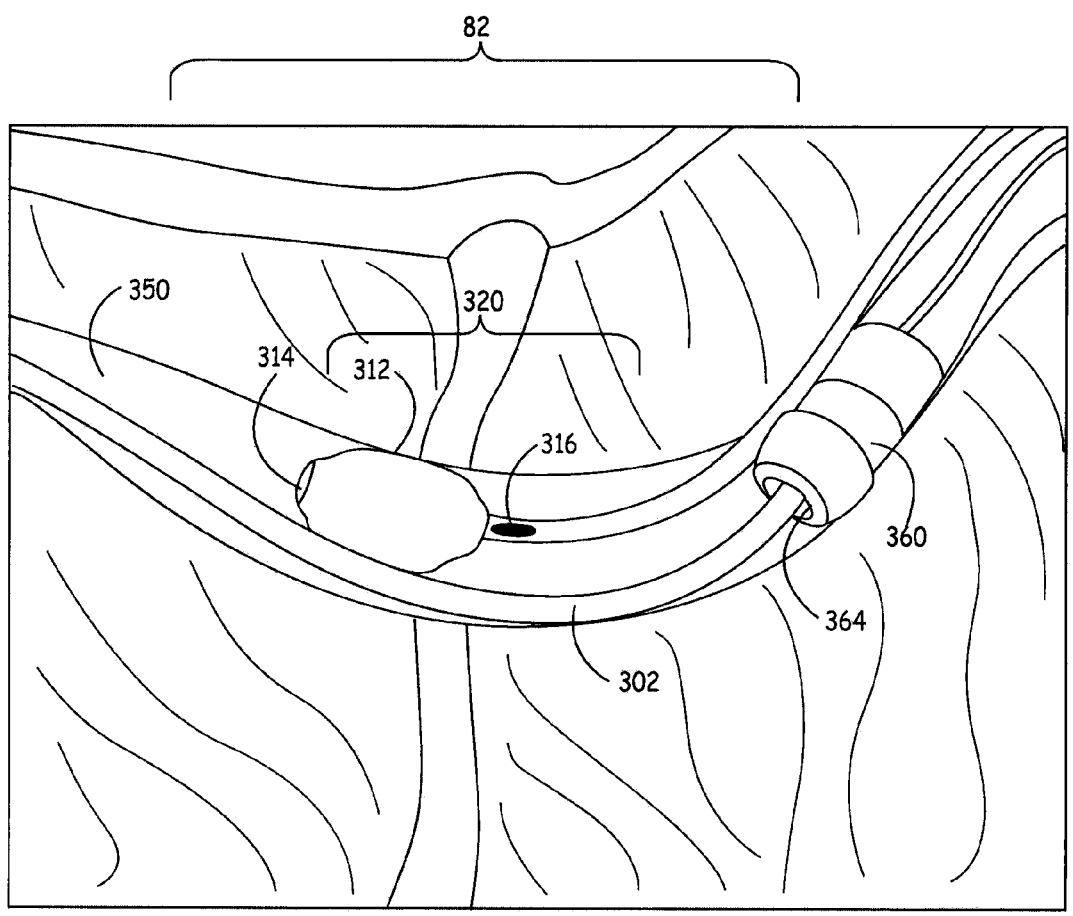
FIG. 21 is an environmental view of a lead delivery device according to various embodiments of the present teachings.
Figure 22:
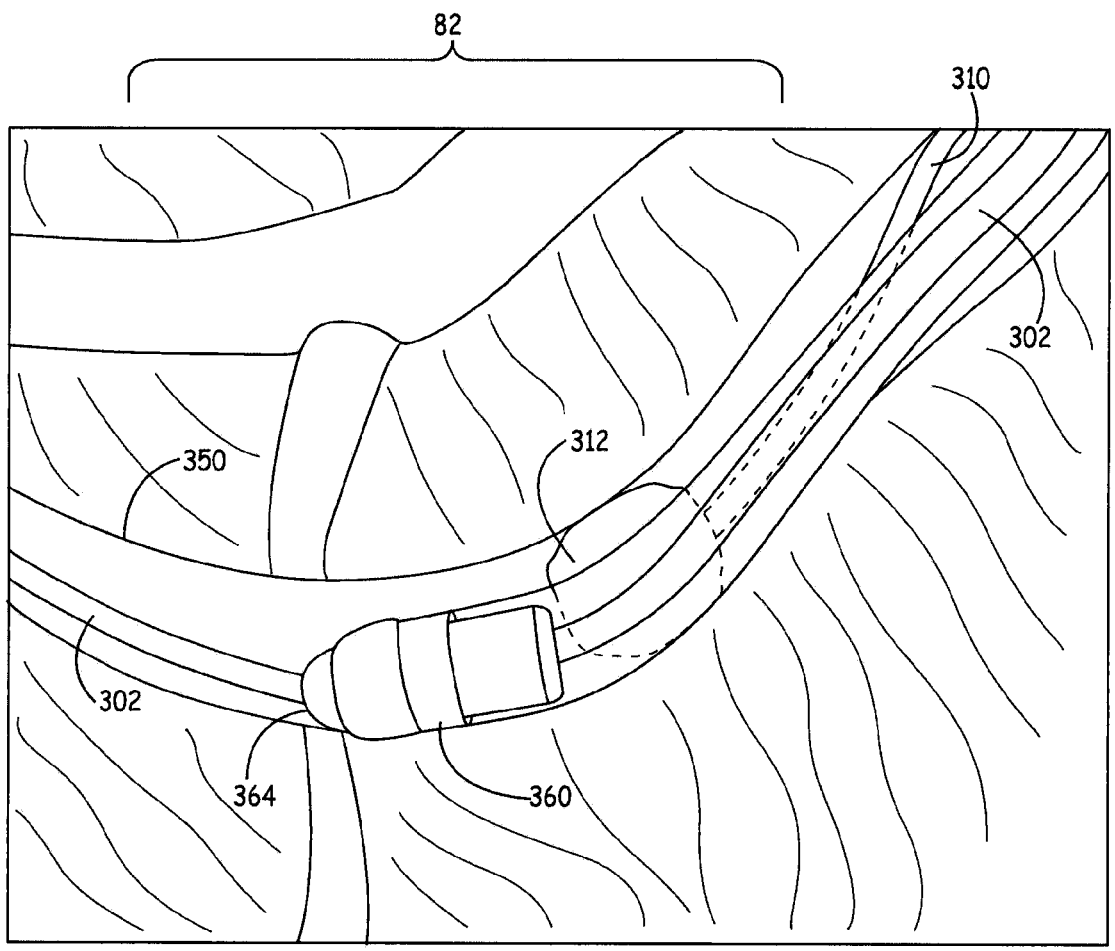
FIG. 22 is an environmental view of a lead delivery device according to various embodiments of the present teachings.

Referring now to FIGS. 21 and 22, a method of finely adjusting the position of guidewire 302 and lead 360 is illustrated. FIG. 21 shows fixator 312 in the expanded condition wherein guidewire 302 is secured between fixator 312 and the wall of blood vessel 350. This is accomplished, for example, by delivering lead delivery device 300 to the desired site 82 and then removing guidewire 302 from distal opening 314 and body opening 316 of fixator catheter 304. The guidewire 302 may be pulled out of communication with fixator catheter 304 by pushing on fixator catheter 304 until the distal portion 342 of guidewire 302 is pulled out of and exits body opening 316. Then, guidewire 302 may be pushed past the distal portion 320 of fixator catheter 304, as illustrated. Fixator 312 may be expanded to secure guidewire 302 against the wall of blood vessel 350 and implantable electrically conductive lead 360 can then be navigated to desired site 82 by, for example, traveling over guidewire 302 through opening 364.

The position of implantable electrically conductive lead 360 and guidewire 302 may be finely adjusted with the selective use of fixator catheter 304. Fixator 312 may be expanded to secure guidewire 302 (as shown in FIG. 21) such that the position of lead 360 may be adjusted. Alternatively, as shown in FIG. 22, fixator catheter 304 may be moved such that fixator 312 is immediately adjacent the body of lead 360. Fixator 312 may then be expanded to secure lead 360 within blood vessel 350. With lead 360 secured, the position of guidewire 302 may be adjusted without the possibility of moving lead 360. In this manner, a user may alternate between securing the guidewire 302 or lead 360 at a certain position, while adjusting unsecured lead 360 or guidewire 302, respectively, and thus more accurately and simply adjust the positioning of lead 360 within desired site 82.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A medical apparatus comprising:
   an electrically conductive lead for a medical device, the lead having an internal bore terminating at a distal lead opening;
   a lead delivery device for delivering the distal end of the lead to a blood vessel during implantation of the lead, the lead delivery device comprising:
   a removably anchorable guidewire; and
   a fixator attached to a distal portion of the guidewire for anchoring the guidewire, the fixator capable of passing through the distal lead opening of the lead; and
   the apparatus further comprising a fixator deployment device, the fixator deployment device capable of deploying the fixator to anchor the guidewire, wherein the fixator deployment device comprises a collapsible sleeve for sealing an inner lumen of the guidewire.

2. The medical apparatus of claim 1, wherein the fixator comprises a at least one expandable lobe.

3. The medical apparatus of claim 1, wherein the fixator comprises a selectively activated portion of the guidewire movable between a compact configuration and an expanded configuration.

4. A medical apparatus comprising:
   an electrically conductive lead for a medical device, the lead having an internal bore terminating at a distal lead opening;
   a lead delivery device for delivering the distal end of the lead to a blood vessel during implantation of the lead, the lead delivery device comprising:
   a removably anchorable guidewire; and
   a fixator attached to a distal portion of the guidewire for anchoring the guidewire, the fixator capable of passing through the distal lead opening of the lead; and
   the apparatus further comprising a fixator deployment device, the fixator deployment device capable of deploying the fixator to anchor the guidewire, wherein the fixator deployment device comprises means for sealing an inner lumen of the guidewire.

5. The medical apparatus of claim 4, wherein the fixator comprises a at least one expandable lobe.

6. The medical apparatus of claim 4, wherein the fixator comprises a selectively activated portion of the guidewire movable between a compact configuration and an expanded configuration.

* * * * *